United States Patent

Eller et al.

[11] Patent Number: 5,877,352
[45] Date of Patent: Mar. 2, 1999

[54] PREPARATION OF AMINES FROM OLEFINS ON BORON-MCM-22 OR ERB-1 ZEOLITES

[75] Inventors: Karsten Eller, Ludwigshafen; Rudolf Kummer, Frankenthal, both of Germany

[73] Assignee: BASF Aktiengesellschaft, Ludwigshafen, Germany

[21] Appl. No.: 978,060

[22] Filed: Nov. 25, 1997

[30] Foreign Application Priority Data

Dec. 3, 1996 [DE] Germany .................. 196 49 946.1

[51] Int. Cl.⁶ .................................................. C07C 209/60
[52] U.S. Cl. .................................................. 564/485
[58] Field of Search ............................... 564/485

[56] References Cited

U.S. PATENT DOCUMENTS

| | | | |
|---|---|---|---|
| 4,375,002 | 2/1983 | Peterson et al. | 564/445 |
| 4,536,602 | 8/1985 | Deeba | 564/485 |
| 4,929,758 | 5/1990 | Taglieber et al. | 564/485 |
| 5,362,697 | 11/1994 | Fung et al. | 502/71 |
| 5,371,310 | 12/1994 | Bennett et al. | 585/467 |
| 5,453,554 | 9/1995 | Cheng et al. | 585/467 |
| 5,648,546 | 7/1997 | Bergfeld et al. | 564/485 |

FOREIGN PATENT DOCUMENTS

| | | |
|---|---|---|
| 2092964 | 3/1993 | Canada . |
| 101 921 | 3/1984 | European Pat. Off. . |
| 133938 | 7/1984 | European Pat. Off. . |
| 132 736 | 2/1985 | European Pat. Off. . |
| 305 564 | 3/1989 | European Pat. Off. . |
| 431451 | 6/1991 | European Pat. Off. . |
| 587 424 | 3/1994 | European Pat. Off. . |
| 590 078 | 9/1995 | European Pat. Off. . |
| 754 676 | 7/1996 | European Pat. Off. . |
| 4206992 | 3/1992 | Germany . |
| 19530177 | 8/1995 | Germany . |

OTHER PUBLICATIONS

Brunet et al., *J. Mol. Catal.,* 49, 1989, pp. 235–259.
Von Lawton et al., *J. Phys. Chem.,* 100, 1996, pp. 3788–3798.
Corma et al. *Stud. Surf. Sci. Catal.,* 37, 1987, pp. 495–503.

*Primary Examiner*—Brian M. Burn
*Attorney, Agent, or Firm*—Keil & Weinkauf

[57] ABSTRACT

A process for preparing amines of the formula I

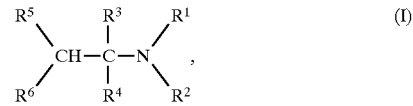

where $R^1, R^2, R^3, R^4, R^5, R^6$ are hydrogen, $C_1$- to $C_{20}$-alkyl, $C_2$- to $C_{20}$-alkenyl, $C_2$- to $C_{20}$-alkynyl, $C_3$- to $C_{20}$-cycloalkyl, $C_4$- to $C_{20}$-alkyl-cycloalkyl, $C_4$- to $C_{20}$-cycloalkyl-alkyl, aryl, $C_7$- to $C_{20}$-alkylaryl or $C_7$- to $C_{20}$-aralkyl, $R^1$ and $R^2$ jointly are a saturated or unsaturated $C_3$- to $C_9$-alkylene divalent chain and $R^3$ or $R^5$ are $C_{21}$- to $C_{200}$-alkyl, $C_{21}$- to $C_{200}$-alkenyl or jointly are a $C_2$- to $C_{12}$-alkylene divalent chain, by reacting olefins of the formula II

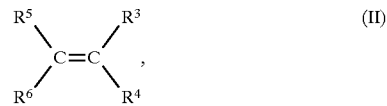

where $R^3$, $R^4$, $R^5$ and $R^6$ have the abovementioned meanings, with ammonia or primary or secondary amines of the formula III

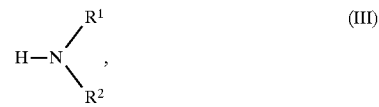

where $R^1$ and $R^2$ have the abovementioned meanings, at from 200° to 350° C. and from 100 to 300 bar in the presence of a heterogeneous catalyst, by using boron-MCM-22 or ERB-1 zeolites as the heterogeneous catalyst.

11 Claims, No Drawings

PREPARATION OF AMINES FROM OLEFINS ON BORON-MCM-22 OR ERB-1 ZEOLITES

The present invention describes a process for preparing amines by reacting ammonia or primary or secondary amines with olefins at elevated temperatures and pressures in the presence of boron-MCM-22 or ERB-1 zeolites.

An overview of the methods for aminating olefins is provided in "Functionalization of Alkenes: Catalytic Amination of Monoolefins", J. J. Brunet et al., J. Mol. Catal., 49 (1989), pp. 235 to 259.

In principle there are two catalytic mechanisms. The olefin is coordinated via a metal complex. This activated species can be attacked by the nucleophilic amine and form a more highly aminated product. The amine can be chemisorbed on acid sites or on metal sites (via metal amides) and thus activated be reacted with the olefin.

Among highly suitable catalysts are zeolites. They are distinguished by their high number of catalytically active sites, in conjunction with a large surface area. The zeolites described differ with respect to type and after treatment (eg. thermal treatment, dealumination, acid treatment, metal ion exchange, etc.). Relevant examples can be found in U.S. Pat. No. 4,375,002, U.S. Pat. No. 4,536,602, EP-A-305 564, EP-A-101 921, DE-A-42 06 992.

EP-A-133 938, EP-A-431 451 and EP-A-132 736 describe processes in which boron zeolites, gallium zeolites, aluminozeolites and iron silicate zeolites are used for preparing amines from olefins and where the possibility of doping these zeolites with alkali metals, alkaline earth metals and transition metals is noted.

CA-A-2 092 964 discloses a process for preparing amines from olefins, which employs BETA zeolites, which are defined as crystalline aluminosilicates of a specific composition having a pore size of more than 5 Å. Preference is given to the use of metal- or halogen-modified beta-zeolites.

All processes for synthesizing amines from olefins on these catalysts are distinguished by a low amine yield or low space-time yield or result in rapid deactivation of the catalysts.

It is therefore an object of the present invention to overcome these drawbacks.

We have found that this object is achieved by a novel and improved process for preparing amines of the formula I

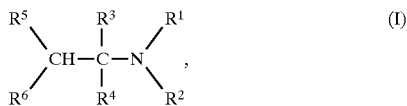

where
R$^1$,R$^2$,R$^3$,R$^4$,R$^5$,R$^6$ are hydrogen, C$_1$- to C$_{20}$-alkyl, C$_2$- to C$_{20}$-alkenyl, C$_2$- to C$_{20}$-alkynyl, C$_3$- to C$_{20}$-cycloalkyl, C$_4$- to C$_{20}$-alkyl-cycloalkyl, C$_4$- to C$_{20}$-cycloalkyl-alkyl, aryl, C$_7$- to C$_{20}$-alkylaryl or C$_7$- to C$_{20}$-aralkyl,
R$^1$ and R$^2$ jointly are a saturated or unsaturated C$_3$- to C$_9$-alkylene divalent chain and
R$^3$ or R$^5$ are C$_{21}$- to C$_{200}$-alkyl, C$_{21}$- to C$_{200}$-alkenyl or jointly are a C$_2$- to C$_{12}$-alkylene divalent chain,
by reacting olefins of the formula II

where R$^3$, R$^4$, R$^5$ and R$^6$ have the abovementioned meanings, with ammonia or primary or secondary amines of the formula III

where R$^1$ and R$^2$ have the abovementioned meanings, at from 200° to 350° C. and from 100 to 300 bar in the presence of a heterogeneous catalyst, wherein the heterogeneous catalyst used comprises boron-MCM-22 or ERB-1 zeolites.

The novel process can be carried out as follows:

The olefin II and ammonia or the primary or secondary amine III can be reacted at from 200° to 350° C., preferably from 220° to 330° C., particularly preferably from 230° to 320° C. and at from 100 to 300 bar, preferably from 120 to 300 bar, particularly preferably from 140 to 290 bar in the presence of boron-MCM-22 or ERB-1 zeolites as a catalyst, eg. in a pressurized reactor, and the amine obtained can be preferentially separated off and the unreacted starting materials be recycled.

The present process is distinguished by a very good yield at high selectivity and high space-time yield. Moreover, the deactivation of the catalyst has been repressed.

The novel process is distinguished by the fact that a small excess of ammonia or amine is sufficient to achieve a high selectivity for the desired reaction product and to avoid the dimerization and/or oligomerization of the olefin employed.

One embodiment of this process comprises ammonia and/or amines III being passed, together with the olefin II, mixed in a molar ratio of from 1:1 to 5:1, to a fixed-bed reactor and being reacted at from 100 to 300 bar and at from 200° to 350° C. in the gas phase or in the supercritical state.

From the reaction output the desired product can be obtained with the aid of known methods, for example distillation or extraction and can, if required, be brought to the desired purity by means of further separation operations. The unreacted starting materials are preferably, as a rule, recycled into the reactor.

The starting materials used can be singly or multiply unsaturated olefins II, in particular those having from 2 to 10 C atoms or mixtures thereof, and polyolefins. Owing to the less pronounced tendency to polymerize, monoolefins are more suitable than di- and polyolefins, although the latter can likewise be reacted selectively with the aid of larger excesses of ammonia or amine. The position of the equilibrium and consequently the conversion ratio to the desired amine depends very markedly on the reaction pressure chosen. A high pressure favors the addition product, although generally, on technical and economic grounds, the pressure range up to 300 bar represents the optimum. The selectivity of the reaction is influenced not only by variables such as the excess of ammonia/amine and the catalyst, but also, largely, by the temperature. While the reaction rate of the addition reaction does increase markedly as the temperature rises, competing cracking and recombination reactions of the olefin are promoted at the same time. Moreover, an increase in temperature is not beneficial, from the thermodynamic point of view. The position of the temperature optimum in terms of conversion ratio and selectivity depends on the constitution of the olefin, of the amine used and of the catalyst and is usually in the range of from 200° to 350° C.

Suitable catalysts for the amination of olefins are boron-MCM-22 zeolites (ERB-1). The boron form of the MCM-22 ([B]-MCM-22) is disclosed, for example, by Leonowicz et al., Science 264 (1994), 1910 to 1913, where the structure of the pore system is also described in more detail. U.S. Pat. No. 4,992,606 describes syntheses of boron-MCM-22 with hexamethylene imine as a template (structure-forming agent). EP-A-293 032 describes the synthesis of a borosilicate with the aid of piperidine as the template, which was subsequently (Millini et al., Microp. Mat. 4 (1995), 221 to 230) described as ERB-1. This zeolite is isostructural with MCM-22, in other words it is [B]-MCM-22 (Perego et al., Microp. Mat. 6 (1996), 395 to 404).

The use as a catalyst in amination reactions does not require all the acidic sites to be generated exclusively by incorporation of trivalent boron into the $SiO_2$ lattice. In addition to boron, a certain proportion of other trivalent ions such as aluminum, gallium or iron may also be present. By varying the ratio of boron to, for example, aluminum it is possible to vary the activity of the catalysts and thus to optimize with respect to the substrate to be employed.

Instead of the trivalent element it is also possible for silicon to be substituted isomorphously by other quadrivalent elements, for example by Ge, Ti or Sn. The molar ratio of $SiO_2$ to $B_2O_3$, the modulus $SiO_2/B_2O_3$, can likewise be varied to influence the activity.

The boron-MCM-22 or ERB-1 zeolites according to the invention can be molded as such or alternatively with a binder in a ratio of from 98:2 to 40:60 wt % to produce extrudates or pellets. Suitable binders include various aluminum oxides, preferably boehmite, amorphous aluminosilicates with an $SiO_2/Al_2O_3$ ratio of from 25:75 to 95:5, silicon dioxide, preferably highly disperse $SiO_2$, mixtures of highly disperse $SiO_2$ and highly disperse $Al_2O_3$, highly disperse $TiO_2$ and clays. After molding, the extrudates or compacts are expediently dried at 110° C./16 hours and calcined at from 200° to 500° C./from 2 to 16 hours, which calcination can also take place directly in the amination reactor.

To increase the selectivity, the on-stream time and the number of possible regenerations it is possible to subject the novel boron-MCM-22 or ERB-1 zeolite catalysts to various modifications.

One modification of the catalysts consists in the option of the zeolites, molded or not molded, being subjected to ion exchange or doped with alkali metals such as Na and K, alkaline earth metals such as Ca, Mg, earth metals such as Tl, transition metals such as eg. Ti, Zr, Mn, Fe, Mo, Cu, Zn, Cr, noble metals and/or rare earth metals such as eg. La, Ce or Y.

An advantageous embodiment comprises the molded boron-MCM-22 or ERB-1 zeolites according to the invention being introduced into a flow tube and having eg. a halide, an acetate, an oxalate, a citrate or a nitrate of the above-described metals in dissolved form passed over them at from 20° to 100° C. An ion exchange of this type can be carried out eg. on the hydrogen form, ammonium form, alkali metal form of the boron-MCM-22 or ERB-1 zeolites according to the invention.

A further option of applying metal to the boron-MCM-22 or ERB-1 zeolites according to the invention consists in the material being impregnated eg. with a halide, an acetate, an oxalate, a citrate, a nitrate or an oxide of the above-described metals in aqueous or alcoholic solution.

Both ion exchange and impregnation can be followed by drying, optionally another calcination. In the case of metal-doped boron-MCM-22 or ERB-1 zeolites an aftertreatment with hydrogen and/or with steam may be beneficial.

A further modification option consists in the boron-MCM-22 or ERB-1 zeolites according to the invention—molded or not molded—being subjected to a treatment with acids such as hydrochloric acid (HCl), hydrofluoric acid (HF), sulfuric acid ($H_2SO_4$), phosphoric acid ($H_3PO_4$), oxalic acid ($HO_2C—CO_2H$) or mixtures thereof.

A particular embodiment comprises the boron-MCM-22 or ERB-1 zeolites according to the invention being treated, prior to molding, with one of said acids, from 0.001N to 2N, preferably from 0.05N to 0.5N, for from 1 to 100 hours under reflux. After filtration and washing, drying takes place as a rule at from 100° to 160° C. and calcination at from 200° to 600° C. A further particular embodiment involves an acid treatment of the boron-MCM-22 or ERB-1 zeolites according to the invention after having been molded with a binder. In the process, the zeolite according to the invention is treated, as a rule, for from 1 to 3 hours at from 60° to 80° C. with a from 3 to 25% strength, in particular a from 12 to 20% strength acid, then washed, dried at from 100° to 160° C. and calcined at from 200° to 600° C. Here, again, calcination can take place directly in the amination reactor.

Another modification option is that of an exchange with ammonium salts, eg. with $NH_4Cl$ or with mono-, di- or polyamines. This involves the zeolite, molded together with binder, being exchanged, as a rule, at from 60° to 80° C. with from 10 to 25% strength, preferably 20% strength $NH_4Cl$ solution continuously for 2 h in a zeolite/ammonium chloride solution of 1:15 by weight and then being dried at from 100° to 120° C.

A further modification to which the boron-MCM-22 or ERB-1 zeolites according to the invention can be subjected is that of deboronation, in which some of the boron atoms are replaced by silicon or the zeolites are depleted, in terms of their boron content, by hydrothermal treatment, for example. A hydrothermal deboronation is advantageously followed by an extraction with acids or complexing agents, to remove any non-lattice boron formed. The replacement of boron by silicon can take place, for example, with the aid of $(NH_4)_2SiF_6$ or $SiCl_4$. Examples of deboronations of β-zeolites can be found in U.S. Pat. No. 4,701,313.

The catalysts can be employed for the amination of the olefins as extrudates having diameters of eg. from 1 to 4 mm or as pellets having a diameter of eg. from 3 to 5 mm.

The catalyst, for example molded into extrudates, can be converted, by grinding and screening, into a fluidizable material having a size of from 0.1 to 0.8 mm.

The substituents $R^1$, $R^2$, $R^3$, $R^4$, $R^5$ and $R^6$ in the compounds I, II and III have the following meanings:

$R^1$, $R^2$, $R^3$, $R^4$, $R^5$, $R^6$ hydrogen, $C_1$- to $C_{20}$-alkyl, preferably $C_1$- to $C_{12}$-alkyl, particularly preferably $C_1$- to $C_8$-alkyl such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl and isooctyl, $C_2$- to $C_{20}$-alkenyl, preferably $C_2$- to $C_{12}$-alkenyl, particularly preferably $C_2$- to $C_8$-alkenyl such as vinyl and allyl, $C_2$- to $C_{20}$-alkynyl, preferably $C_2$- to $C_8$-alkynyl, in particular $C_2H$ and propargyl, $C_3$- to $C_{20}$-cycloalkyl, preferably $C_3$- to $C_{12}$-cycloalkyl, particularly preferably $C_5$- to $C_8$-cycloalkyl such as cyclopentyl, cyclohexyl, cycloheptyl and cyclooctyl, $C_4$- to $C_{20}$-alkyl-cycloalkyl, preferably $C_4$- to $C_{12}$-alkyl-cycloalkyl, particularly preferably $C_5$- to $C_{10}$-alkyl-cycloalkyl, $C_4$- to $C_{20}$-cycloalkyl-alkyl, preferably $C_4$- to $C_{12}$-cycloalkyl-alkyl, particularly preferably $C_5$- to $C_{10}$-cycloalkyl-alkyl, aryl such as phenyl, 1-naphthyl and 2-naphthyl, preferably phenyl, $C_7$- to $C_{20}$-alkylaryl, preferably $C_7$- to $C_{16}$-alkylaryl, particularly preferably $C_7$- to $C_{12}$-alkylphenyl such as 2-methylphenyl, 3-methylphenyl, 4-methylphenyl, 2-ethylphenyl, 3-ethylphenyl and 4-ethylphenyl, $C_7$- to $C_{20}$-aralkyl, preferably $C_7$- to $C_6$-aralkyl, particularly preferably $C_7$- to $C_{12}$-phenalkyl such as phenylmethyl, 1-phenylethyl, 2-phenylethyl, $R^1$ and $R^2$ jointly a saturated or unsaturated $C_3$- to $C_9$-alkylene divalent chain, preferably —$(CH_2)_4$—, —$(CH_2)_5$—, —$(CH_2)_7$— and —CH=CH—CH=CH—, $R^3$ or $R^5$ $C_{21}$- to $C_{200}$-alkyl, preferably $C_{40}$- to $C_{200}$-alkyl, such as polybutyl, polyisobutyl, polypropyl, polyisopropyl and polyethyl, particularly preferably polybutyl and polyisobutyl, $C_{21}$- to $C_{200}$-alkenyl, preferably $C_{40}$- to $C_{200}$-alkenyl, particularly preferably $C_{70}$- to $C_{170}$-alkenyl, $R^3$ and $R^5$ jointly a $C_2$- to $C_{12}$-alkylene divalent chain, preferably a $C_3$- to $C_8$-alkylene divalent chain, particularly preferably —$(CH_2)_3$—, —$(CH_2)_4$—, —$(CH_2)_5$—, —$(CH_2)_6$— and —$(CH_2)_7$—, in particular —$(CH_2)_3$— and —$(CH_2)_4$—.

EXAMPLES

Catalyst Syntheses

Catalyst A: Na-[B]-MCM-22 (Na-ERB-1)

A stirred flask fitted with a reflux condenser was charged with 182.4 g of water and 16.2 g of NaOH, 85.8 g of piperidine were added and the mixture was then heated to 50° C. After addition of 83.55 g of boric acid the temperature was raised to 70° C. and the contents were stirred until the boric acid had completely dissolved. Within an hour, 152.1 g of Ludox® AS 40 ($SiO_2$, from Dupont) were then added and the mixture was stirred for a further 1 h at 70° C. The resulting gel was transferred in equal parts into two 300 ml autoclaves and crystallized at 155° C. for 14 days under intrinsic pressure without stirring. The zeolite formed was filtered off and washed, dried for 16 h at 120° C. and calcined for 5 h at 550° C. The analysis of their diffractogram indicated the formation of ERB-1 ([B]-MCM-22). The module ($SiO_2/Al_2O_3$) was 21.

Catalyst B: Na-[B]-MCM-22 (Na-ERB-1)

50 g of catalyst A were compacted in a kneader with 34 g of boehmite and 1.7 g of formic acid and were kneaded for 60 min with the addition of water (52 ml). An extruder was used, with an extrusion pressure of 75 bar, to produce 2 mm extrudates which were dried for 4 h at 120° C. and calcined for 16 h at 500° C. Sodium analysis revealed a value of 1.0%.

Catalyst C: H-[B]-MCM-22 (H-ERB-1)

38 g of catalyst B were placed into a double-walled glass tube which was heated to 80° C. by means of a thermostat. 1 kg of a 20% strength $NH_4Cl$ solution was recirculated through the tube for 2 h pumping. This was followed by washing with 5 l of distilled water, the $NH_4Cl$ exchange was repeated, 10 l of water were used for washing, and the zeolite was dried for 4 h at 120° C. and calcined for 5 h at 500° C. The entire procedure was then repeated once more. The sodium analysis gave a value of 0.57%.

Catalyst D: H-[B]-MCM-22 (H-ERB-1)

18 g of catalyst A were stirred with 270 g of a 20% strength $NH_4Cl$ solution for 2 h at 80° C. and then filtered off and washed with 3 l of water. After renewed $NH_4Cl$ exchange and rewashing with 3 l of water, the zeolite was dried for 2 h at 120° C. and calcined for 5 h at 500° C. The entire procedure was then repeated once more. The sodium analysis gave a value of 0.48%.

17 g of exchanged zeolite were compacted in a kneader with 7 g of boehmite and 1 ml of formic acid and were kneaded for 45 min with the addition of water (18 ml). A hand press was used to produce 2 mm extrudates which were dried for 4 h at 120° C. and calcined for 16 h at 500° C. The sodium analysis gave a value of 0.33%.

Catalyst E: K-[B]-MCM-22

5.18 g of boric acid and 2 g of KOH (45%) were dissolved in 85.9 g of water, followed by the addition of 17.2 g of Aerosil® 50 (from Degussa). After addition of 7.76 g of hexamethylene imine the gel being formed is transferred into an autoclave and crystallized at 150° C. for 21 days under intrinsic pressure with stirring. The zeolite formed was filtered off and washed, dried for 16 h at 120° C. and calcined for 6 h at 540° C. The analysis of the diffractogram indicated the formation of [B]-MCM-22. The synthesis was repeated four more times with the same result.

Catalyst F: H-[B]-MCM-22

80 g of catalyst E (module $SiO_2/Al_2O_3$=23) were stirred with 1500 g of a 20% strength $NH_4Cl$ solution for 2 h at 80° C. and then filtered off and washed with 5 l of water. After renewed $NH_4Cl$ exchange and rewashing, the zeolite was dried for 4 h at 120° C. and calcined for 4 h at 500° C. The entire procedure was then repeated once more.

60 g of the exchanged zeolite were compacted in a kneader with 40 g of boehmite and 2 g of formic acid and were kneaded for 60 min with the addition of water (105 ml). An extruder was used, with an extrusion pressure of 50 bar, to produce 2 mm extrudates which were dried for 4 h at 120° C. and calcined for 16 h at 500° C. Potassium analysis revealed a value of 0.32%.

20 g of catalyst B were treated for 24 hours with 100 ml of conc. $HNO_3$ at 110° C., followed by drying for 4 hours at 120° C. and calcining for 5 hours at 500° C. Sodium analysis revealed a value of 0.93%.

Amination Examples

The experiments were carried out in a tubular reactor (internal diameter 6 mm) under isothermal conditions at from 260° to 300° C. and at 280 bar, using a mixture of isobutene and ammonia in a molar ratio of 1:1.5. The reaction products were analyzed in a gas chromatograph.

The results are summarized in Table 1.

TABLE 1

| Catalyst | Tempera-ture [°C.] | Yield of t-butylamine [wt %] | | | Weight per liter [kg/l] |
| --- | --- | --- | --- | --- | --- |
| | | WHSV 0.75 [g/g · h] | WHSV 1.5 [g/g · h] | WHSV 3 [g/g · h] | |
| B | 270 | 16.37 | 11.35 | 8.09 | 0.58 |
| B | 280 | 18.08 | 15.53 | 11.17 | 0.58 |
| B | 300 | | | 13.27 | 0.58 |
| C | 270 | 19.39 | 12.90 | 8.29 | 0.58 |
| C | 280 | 17.97 | 15.11 | 11.17 | 0.58 |
| C | 300 | | | 12.57 | 0.58 |
| D | 270 | 14.99 | 9.72 | 5.93 | 0.58 |
| F | 270 | 13.40 | 7.75 | 4.63 | 0.41 |
| G | 270 | | 11.69 | 7.84 | |

We claim:
1. A process for preparing amines of the formula I

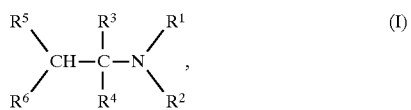

where
R¹,R²,R³,R⁴,R⁵,R⁶ are hydrogen, $C_1$- to $C_{20}$-alkyl, $C_2$- to $C_{20}$-alkenyl, $C_2$- to $C_{20}$-alkynyl, $C_3$- to $C_{20}$-cycloalkyl, $C_4$- to $C_{20}$-alkyl-cycloalkyl, $C_4$- to $C_{20}$-cycloalkyl-alkyl, aryl, $C_7$- to $C_{20}$-alkylaryl or $C_7$- to $C_{20}$-aralkyl, R¹ and R² jointly are a saturated or unsaturated $C_3$- to $C_9$-alkylene divalent chain and
R³ or R⁵ are $C_{21}$- to $C_{200}$-alkyl, $C_{21}$- to $C_{200}$-alkenyl or jointly are a $C_2$- to $C_{12}$-alkylene divalent chain,
by reacting olefins of the formula II

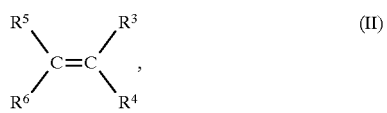

where R³, R⁴, R⁵ and R⁶ have the abovementioned meanings, with ammonia or primary or secondary amines of the formula III

where R¹ and R² have the abovementioned meanings, at from 200° to 350° C. and from 100 to 300 bar in the presence of a heterogeneous catalyst, wherein the heterogeneous catalyst used comprises boron-MCM-22 or ERB-1 zeolites.

2. A process for preparing amines I as claimed in claim 1, wherein the amine I formed is separated off and the unreacted starting materials II and III are recycled.

3. A process for preparing amines as claimed in claim 1, wherein the olefin II used is isobutene, diisobutene, cyclopentene, cyclohexene or polyisobutene.

4. A process for preparing amines as claimed in claims 1, wherein the heterogeneous catalysts used comprise boron-MCM-22 or ERB-1 zeolites in the H form.

5. A process for preparing amines as claimed in claim 1, wherein the heterogeneous catalysts used comprise boron-MCM-22 or ERB-1 zeolites which have been treated with an acid, in particular an acid from the group consisting of hydrochloric acid, hydrofluoric acid, sulfuric acid, phosphoric acid, oxalic acid or mixtures thereof.

6. A process for preparing amines as claimed in claim 1, wherein the heterogeneous catalysts used comprise boron-MCM-22 or ERB-1 zeolites which are doped with one or more transition metals.

7. A process for preparing amines as claimed in claim 1, wherein the heterogeneous catalysts used comprise boron-MCM-22 or ERB-1 zeolites which are doped with one or more rare earth elements.

8. A process for preparing amines as claimed in claim 1, wherein the heterogeneous catalysts used comprise boron-MCM-22 or ERB-1 zeolites in the ammonium form.

9. A process for preparing amines as claimed in claim 1, wherein the heterogeneous catalysts used comprise boron-MCM-22 or ERB-1 zeolites which are doped with one or more elements from the group consisting of the alkali metals, alkaline earth metals or earth metals.

10. A process for preparing amines as claimed in claim 1, wherein the heterogeneous catalysts used comprise boron-MCM-22 or ERB-1 zeolites which have been molded with a binder and calcined at from 200° to 600° C.

11. A process for preparing amines as claimed in claim 1, wherein the heterogeneous catalysts used comprise deboronated boron-MCM-22 or ERB-1 zeolites.

* * * * *